United States Patent [19]
Kikuchi et al.

[11] Patent Number: 5,993,863
[45] Date of Patent: Nov. 30, 1999

[54] ALIMENTATIVE INFUSION LIQUIDS FOR ADMINISTRATION THROUGH PERIPHERAL VEIN

[75] Inventors: Masahiro Kikuchi; Yoshihiko Okutani; Tadaaki Inoue; Ryoichiro Murashima; Shunichi Abe, all of Osaka; Hiroshi Koshiba, Hyogo; Hiroshi Shibata, Hyogo; Shunichiro Ishii, Hyogo; Yoshiyasu Kawabata, Hyogo; Kazumasa Yokoyama, Osaka, all of Japan

[73] Assignee: Yoshitomi Pharmaceutical Industries, Ltd., Osaka, Japan

[21] Appl. No.: 08/946,359

[22] Filed: Oct. 7, 1997

Related U.S. Application Data

[63] Continuation of application No. 08/537,894, filed as application No. PCT/JP94/00713, Apr. 27, 1994.

[30] Foreign Application Priority Data

Apr. 30, 1993 [JP] Japan .................................... 5-127864

[51] Int. Cl.[6] .......................... A61K 33/42; A61K 33/32; A61K 33/14; A61K 33/06; A61K 31/70
[52] U.S. Cl. .......................... 424/602; 424/641; 424/677; 424/682; 514/23; 514/400; 514/561; 514/565; 514/566
[58] Field of Search ...................................... 424/602, 641, 424/677, 682; 514/23, 561, 400, 565, 566

[56] References Cited

U.S. PATENT DOCUMENTS 4,920,098  4/1990  Cotter et al. ................................ 514/2

FOREIGN PATENT DOCUMENTS

| 0 510 687 A2 | 10/1992 | European Pat. Off. . |
| 0 510 687 A3 | 10/1992 | European Pat. Off. . |
| 5-32540 | 2/1993 | Japan . |

OTHER PUBLICATIONS

Parry et al., "Effect of Various Nutrient Ratios on the Emulsion Stability of Total Nutrient Admixtures" Am. J. of Hospital Pharmacy, 43:3017–3022 (1986).

*Primary Examiner*—Raymond Henley, III
*Attorney, Agent, or Firm*—Sughrue, Mion, Zinn, Macpeak & Seas, PLLC

[57] ABSTRACT

The present invention aims at providing an alimentative infusion liquid which has improved stability and preservability and can be administered through a peripheral vein. The infusion liquid contains sugars, amino acids, electrolytes and a fat emulsion at a specific mixing ratio and has a specific pH value and a titratable acidity. The alimentative infusion liquid of the present invention containing the above-described components has good preservability without suffering from precipitation, denaturation and the like problems. Further, since the pH value is adjusted to a specific level and the titratable acidity is retained low, administration of the infusion liquid through a peripheral vein does not cause troubles such as angialiga.

10 Claims, 1 Drawing Sheet

ALIMENTATIVE INFUSION LIQUIDS FOR ADMINISTRATION THROUGH PERIPHERAL VEIN

This is a continuation of application Ser. No. 08/537,894 filed Oct. 25, 1995.

TECHNICAL FIELD

This invention relates to an alimentative infusion liquid to be administered via a peripheral vein. More particularly, it relates to an infusion liquid to be administered via a peripheral vein which is a hyperalimentative infusion liquid containing sugars, amino acids, electrolytes and a fat emulsion, having an excellent stability and causing no trouble such as angialgia during the administration.

BACKGROUND ART

Intravenous infusion is carried out for the purpose of supplying nutrients to maintain a patient's life when oral or nasal feeding is impossible or insufficient, when the digestion and absorption functions of the patient are in a poor state, even if such a feeding means can be carried out, or when the passage of food through the digestive tract makes the patient's condition or disease more serious. Examples of commercially available infusion preparations include a sugar intravenous infusion liquid which contains reducing sugars and the like, an amino acid intravenous infusion liquid which contains essential amino acids and the like, an electrolyte infusion liquid which contains minerals and the like, a fat emulsion which contains a plant oil emulsion and the like, and a vitamin mixture. These infusion preparations are appropriately selected depending on the condition of the patient and are mixed upon use. However, mixing these preparations at the time of their use requires complex handling and, above all things, raises the problem of microbial contamination. With the aim of overcoming such problems, various infusion preparations, in which some of the aforementioned infusion liquids are mixed in advance, have been proposed. Infusion preparations which contain sugars, amino acids, electrolytes and a fat emulsion, all being essential nutrients to be supplied, are especially useful from a clinical point of view.

However, since these sugar infusion liquids, amino acid infusion liquids, electrolyte infusion liquids and fat emulsion are different from one another in terms of the conditions for their stable existence, various problems arise when they are mixed, and the mixture becomes useless in many cases.

For example, because of its unstable nature, a fat emulsion is apt to form bulky fat particles and to cause phase separation (creaming) when mixed with other infusion liquids. In particular, divalent cations contained in an electrolyte infusion liquid cause aggregation and disintegration of fat emulsion particles.

In the case of an electrolyte infusion liquid, since it contains calcium and phosphoric acid as essential components to maintain the balance of electrolytes, it is apt to form calcium phosphate by the reaction of calcium with phosphoric acid and thereby to generate turbidity and precipitation. In order to prevent the formation of turbidity and precipitation, such an electrolyte infusion liquid is usually adjusted to a low pH value (less than pH 5). When such a electrolyte infusion liquid is mixed with an amino acid infusion liquid, the pH of the mixture increases to the amino acid pH value because of the strong buffer action of amino acids, thus requiring a large quantity of acidic materials (for example, hydrochloric acid, acetic acid and the like) to keep the pH value at a low level. However, acidic materials can be used only in a limited amount because a large quantity of acid spoils the balance of the infusion components. As a consequence, the pH value of the mixture of electrolyte and amino acid infusion liquids cannot be lowered to a satisfactory level, thus resulting in the generation of turbidity and precipitation during heat sterilization of the mixture.

In addition, when a mixture of an amino acid infusion liquid with a sugar infusion liquid is sterilized by heating, it is known that considerable coloring occurs due to the Maillard's reaction.

As described above, it is difficult to prepare a storable infusion preparation which contains a sugar, amino acids, electrolytes and a fat emulsion, in advance, because mixing these different types of infusion liquids or emulsions causes various problems such as precipitation, phase separation, denaturation, coloring and the like. Because of these problems, a fat emulsion, a sugar infusion liquid, an amino acid infusion liquid and an electrolyte infusion liquid are ordinarily mixed upon use. As a consequence, an alimentative infusion liquid has been desired which contains sugars, amino acids, electrolytes and a fat emulsion and can be stably stored.

There has been required a convenient method for complete alimentation via a peripheral vein in institutions where total intravenous alimentation is scarcely employed. Also, alimentation via a peripheral vein is a preferable method in order to completely feed a patient with temporary cut-off of oral alimentation for a short period of time. However, conventional alimentative infusion liquids to be administered via a peripheral vein have a low caloric value. For the total alimentation, it is therefore necessary to administer such an infusion liquid in an increased dose. However, an increase in the administration dose is accompanied by troubles such as angialgia and phlebitis, which restricts the administration dose. Thus, it is impossible to supply a sufficient energy to a patient, which makes the patient undernourished. Under such conditions, there is a risk that the patient suffers from unfavorable symptom. On the other hand, the injection of a common infusion liquid, which is to be administered via the main vein, into a peripheral vein causes side effects such as angialgia. Thus such an infusion liquid cannot be administered via a peripheral vein in practice.

Accordingly, it has been urgently required to develop a hyperalimentative infusion liquid which can be administered via a peripheral vein and enables total alimentation.

Under these circumstances, the present inventors have conducted extensive studies on an alimentative infusion liquid containing sugars, amino acids, electrolytes and a fat emulsion, which is stable and can be administered via a peripheral vein. As a result, they have successfully found out that an alimentative infusion liquid containing the above-mentioned components, which is free from various problems, for example, precipitation, phase separation, denaturation and coloring, and can be administered via peripheral vein without any trouble, can be obtained by improving the properties of each component, the composition and the liquid properties, thus completing the present invention. Accordingly, an object of the present invention is to provide an alimentative infusion liquid containing sugars, amino acids, electrolytes and a fat emulsion, which is hyperalimentative, excellent in stability and preservability and can be administered via a peripheral vein.

DISCLOSURE OF THE INVENTION

The alimentetive infusion liquid of the present invention to be administered via a peripheral vein, which aims at solving the above-mentioned problems, comprises sugars, amino acids, electrolytes and a fat emulsion, contains the following components, and has a pH value of from 6.3 to 7.3 and a titratable acidity of 8.5 mEq/l or below.

| | |
|---|---|
| fat | 30–40 g/l |
| emulsifying agent | 4–6 g/l |
| sugar | 60–90 g/l |
| L-isoleucine | 1–3 g/l |
| L-leucine | 2.5–4.5 g/l |
| L-valine | 1–3 g/l |
| L-lysine | 1–3 g/l |
| L-methionine | 0.5–1.5 g/l |
| L-phenylalanine | 1–3 g/l |
| L-threonine | 0.5–2.5 g/l |
| L-tryptophan | 0.1–1 g/l |
| L-arginine | 1.5–3.5 g/l |
| L-histidine | 0.5–2.5 g/l |
| glycine | 0.5–2.5 g/l |
| L-alanine | 1–3 g/l |
| L-proline | 0.5–2.5 g/l |
| L-aspartic acid | 0.1–1 g/l |
| L-serine | 0.1–2 g/l |
| L-tyrosine | 0.05–0.25 g/l |
| L-glutamic acid | 0.3–0.6 g/l |
| L-cysteine | 0.01–0.5 g/l |
| sodium | 30–40 mEq/l |
| potassium | 15–25 mEq/l |
| calcium | 1–5 mEq/l |
| magnesium | 1–5 mEq/l |
| chlorine | 25–30 mEq/l |
| phosphorus | 5–15 mmol/l |
| zinc | 1–10 μmol/l |
| acetic acid | 15–35 mEq/l |

In particular, the fat emulsion preferably has a mean particle diameter of 0.17 μm or less. The electrolytes preferably contains a phosphoric ester of a polyhydric alcohol or a sugar or a salt of the ester as a source of phosphorus.

According to the present invention comprising the above-described constitution, various types of sugars may be used as sugars. Reducing sugars are preferably used. Examples of the reducing sugars include glucose, fructose, maltose and the like. These reducing sugars may be used as a mixture of two or more. These reducing sugars may be mixed further with sorbitol, xylitol, glycerol and the like.

Examples of the amino acids include various amino acids (essential and non-essential amino acids) which have been used in conventional amino acid infusion preparations for supplying the living body with- nutrients, such as L-isoleucine, L-leucine, L-valine, L-lysine, L-methionine, L-phenylalanine, L-threonine, L-tryptophan, L-arginine, L-histidine, glycine, L-alanine, L-proline, L-aspartic acid, L-serine, L-tyrosine, L-glutamic acid, L-cysteine and the like. These amino acids may be used, not only as free amino acid forms, but also in various other forms which include for instance: inorganic acid salts (e.g., L-lysine hydrochloride, etc.); organic acid salts (e.g., L-lysine acetate, L-lysine malate, etc.); esters which can be hydrolyzed in vivo (e.g., L-tyrosine methyl ester, L-methionine methyl ester, L-methionine ethyl ester, etc.); N-substituted derivatives (e.g., N-acetyl-L-tryptophan, N-acetyl-L-cysteine, N-acetyl-L-proline, etc.); and dipeptides of the same or different amino acids (e.g., L-tyrosyl-L-tyrosine, L-alanyl-L-tyrosine, L-arginyl-L-tyrosine, L-tyrosyl-L-arginine, etc.).

Various types of water soluble salts which have been used in the prior art infusion preparations can be used as electrolytes, including water soluble salts (e.g., chlorides, sulfates, acetates, gluconates, lactates, etc.) of various inorganic components which are considered to be essential for the maintenance of biological functions and electrolyte balance in the body fluid (e.g., sodium, potassium, calcium, magnesium, zinc, iron, copper, manganese, iodine, phosphorus, etc.). Hydrates of these water soluble salts may also be used.

In these electrolyte components, phosphoric esters of polyhydric alcohols or sugars or salts thereof are used suitably as the source of phosphorus. Examples of phosphoric esters of polyhydric alcohols include glycerophosphoric acid, mannitol-1-phosphoric acid, sorbitol-1-phosphoric acid and the like. Examples of phosphoric esters of sugars include glucose-6-phosphoric acid, fructose-6-phosphoric acid and mannose-6-phosphoric acid and the like. As salts of these phosphoric esters, alkali metal salts such as sodium salt, potassium salt and the like may be used. Preferred phosphoric ester salts include a sodium salt and a potassium salt of glycerophosphoric acid.

The preferred electrolyte components include the following compounds:

Sodium: sodium chloride, sodium lactate, sodium acetate, sodium sulfate and sodium glycerophosphate;

Potassium: potassium chloride, potassium glycerophosphate, potassium sulfate, potassium acetate and potassium lactate;

Calcium: calcium gluconate, calcium chloride, calcium glycerophosphate, calcium lactate, calcium pantothenate and calcium acetate;

Magnesium: magnesium sulfate, magnesium chloride, magnesium glycerophosphate, magnesium acetate and magnesium lactate;

Phosphorus: potassium glycerophosphate, sodium glycerophosphate, magnesium glycerophosphate and calcium glycerophosphate; and.

Zinc: zinc sulfate, zinc chloride, zinc gluconate, zinc lactate and zinc acetate.

The fat emulsion of the present invention may be an oil-in water type emulsion which is prepared by dispersing a fat in water using an emulsifying agent. The fat emulsion may be prepared in a conventional manner, for example, by adding a fat and an emulsifying agent to water, stirring the mixture to prepare a crude emulsion and then emulsifying the crude emulsion by any commonly used means such as by a high pressure emulsification method.

Any edible fats and oils can be used as the fat source of the fat emulsion. Preferably used are one or more fats and oils selected from the group consisting of plant oils (e.g., soybean oil, cottonseed oil, safflower oil, corn oil, coconut oil, Perilla frutescens oil, perilla oil, etc.); fish oils (e.g., cod liver oil, etc.); medium-chain fatty acid triglycerides [e.g., Panacet (trade name), ODO (trade name), etc. ]; and chemically synthesized triglycerides [e.g., chemically defined triglycerides, such as 2-linoleoyl-1,3-dioctanoyl glycerol (8L8), 2-linoleoyl-1,3-didecanoyl glycerol (10L10), etc.].

Any emulsifying agent commonly used in pharmaceutical preparations may be used in the present invention. One or more agents may be used which are preferably selected from the group consisting of egg yolk phospholipids, hydrogenated egg yolk phospholipids, soybean phospholipids, hydrogenated soybean phospholipids and nonionic surface active agents [e.g., Pluronic F68 (trade name) and HCO-60 (trade name), etc.].

A soybean oil and egg yolk phospholipid are particularly preferred as the fat source and as the emulsifying agent, respectively, to prepare a fat emulsion.

According to the present invention, the fat emulsion may preferably be prepared so that its mean particle diameter becomes 0.17 μm or less. By controlling the particle diameter at this level, higher stability of the fat emulsion than those of currently used fat emulsions (mean particle diameter ranging from 0.2 to 0.3 μm) can be achieved and phase separation in the fat emulsion caused by a difference in specific gravities can be effectively prevented.

A fat emulsion having a mean particle diameter of 0.17 μm or less can be prepared by adding one or more of the compounds selected from glycerol and glucose, followed by emulsification. The conventionally used emulsification method comprises adding a fat and an emulsifying agent to water, stirring the mixture to prepare a crude emulsion, and then emulsifying the crude emulsion by any commonly used means such as a high pressure emulsification method. According to this method, it is difficult to obtain a fat emulsion having a mean particle diameter of 0.2 μm or less. The present inventors have found that glycerol and glucose have a specific capacity to make particles smaller. According to the above production method, a fat emulsion having a mean particle diameter of 0.17 μm or less can be prepared easily.

More illustratively, such a fat emulsion can be prepared, for example, by adding a fat source and an emulsifying agent to water, together with one or more compounds selected from glycerol and glucose, stirring the mixture to obtain a crude emulsion, and then emulsifying the crude emulsion by a conventional method such as a high pressure emulsification method. When the emulsion is prepared by the high pressure emulsification method, the crude emulsion may be passed 5 to 50 times through a homogenizer such as a Manton-Gaulin homogenizer at a pressure condition of generally from 20 to 700 kg/cm$^2$. In this instance, glycerol and/or glucose may be added at the time of the emulsification. For example, glycerol and/or glucose may be added to a crude emulsion prepared from a fat and an emulsifying agent to further conduct emulsification.

The mean particle diameter of the thus prepared emulsion can be determined by a conventional method such as a light scattering method.

In the above-described emulsion preparation method, a fat, an emulsifying agent and glycerol and/or glucose may be used in such amounts that the resulting fat emulsion consists of the fat in an amount of from 0.1 to 30 w/v % (unless otherwise noted, the term "%" as used hereinafter means w/v %), preferably from 1 to 20%, the emulsifying agent in an amount of from 0.01 to 10%, preferably from 0.05 to 5%, the glycerol and/or glucose in an amount of from 30 to 70%, preferably from 40 to 60%, and water in an appropriate amount.

The type, mixing ratio and concentration of sugars, amino acids, electrolytes and a fat emulsion to be used in the alimentative infusion liquid of the present invention may vary depending on use, diseases of the patient and symptoms, within the above-described composition range.

The alimentative infusion liquid of the present invention can be obtained by dissolving or dispersing each of the above-described components in purified water (for example, water for injection, etc.). Preferably, a sugar infusion liquid, an amino acid infusion liquid, an electrolyte infusion liquid and a fat emulsion are prepared independently and sterilized, for example, by heating, and an appropriate amount of each of the infusion liquids is mixed aseptically to give a desired concentration of each component.

The above-described sugar infusion liquid, amino acid infusion liquid and electrolyte infusion liquid can be prepared by a conventional method and the fat emulsion can be prepared by the above-described method. Each infusion liquid thus prepared is packed into a container (e.g., bag, bottle, etc.) made of glass or plastic (e.g., polypropylene, polyethylene, ethylene-vinyl acetate copolymer, polyvinylchloride, etc.). After air in the container is replaced with inert gas (e.g., nitrogen gas, helium gas, etc.), the container is sealed and subjected to sterilization. The sterilization may be effected in a common way, for example, by a heat sterilization treatment such as high-pressure steam sterilization, hot water immersion sterilization, hot water shower sterilization or the like. When a plastic container is used, sterilization is preferably carried out in the atmosphere substantially free from oxygen.

Alternatively, the alimentative infusion liquid of the present invention can be prepared using a sealed container having two compartments separated from each other by a separation means which is formed by heat fusion so that it can be peeled. Specifically, the infusion liquid can be prepared by introducing an infusion liquid containing a fat emulsion and sugars in the first compartment, introducing an infusion liquid containing amino acids and electrolytes in the second compartment, sterilizing the container by heating, peeling the separation means to connect the first compartments and the second compartment and mixing both infusion liquids.

The present invention is illustrated in more detail with reference to FIG. 1 showing a cross-sectional figure of a container used in the practice of the above-described method. In this figure, a container 1 is made of a flexible material such as plastic film and has two compartments, that is, a first compartment 3 and a second compartment 4 which are separated from each other by a separation part 2 formed by fusing the film constituting the container 1. The separation part 2 is formed so that it can be peeled by applying external power (for example, a method of pressing one of the compartments, a method of peeling the separation part and the like). The first compartment 3 contains an infusion liquid 5 containing a fat emulsion and sugars and the second compartment 4 contains another infusion liquid 6 containing amino acids and electrolytes. Since the first compartment 3 and the second compartment 4 are separated from each other by the separation part 2, the infusion liquid 5 enclosed in the first compartment 3 cannot be mixed with the infusion liquid 6 enclosed in the second compartment 4. In addition, the container 1 is equipped with a port 7 for use in the injection of the infusion liquid 5 into the first compartment 3 and a port 8 for use in the injection of the infusion liquid 6 into the second compartment 4.

Examples of the plastic materials to be used for the container 1 include various plastic materials conventionally used for the container for the infusion liquids, such as polyethylene, polypropylene, polyester, polyvinylalcohol, polyamide, polyurethane, ethylene-vinyl acetate copolymer and the like. In particular, a laminated film or sheet composed of the above-described materials is suitably used.

The method of producing the container for the infusion liquids shown in FIG. 1 is illustrated below. The separation part 2 is made by heat fusion of the container 1, an infusion liquid is injected into either of the first compartment 3 or the second compartment 4 which is separated from each other by the separation part 2 through the port and the port is sealed. Then, the container is reversed and another infusion liquid is injected into the other compartment through the port followed by sealing the port In this instance, air of the each compartment filled with the infusion liquid is preferably substituted with inert gas (for example, nitrogen gas). More preferably, the injection of the infusion liquid into each compartment is carried out under a stream of inert gas (for example, nitrogen gas).

The container 1 filled with the infusion liquids is subjected to heat sterilization in accordance with the conventional method to obtain the container 1 filled with the infusion liquid.

The separation part 2 of the container filled with the infusion liquids shows in FIG. 1 is peeled by external power upon use to become open, thereby mixing the infusion liquids contained in the first compartment 3 and the second compartment 4. Then, the mixed infusion liquid is ejected from the port 7 through a tube (not shown) to administer it to the living body aseptically. If necessary, other drugs can be introduced through the port 7 or 8.

The heat sterilized container 1 filled with the infusion liquids may be made into a double package by putting the container into a bag made of an oxygen-impermeable plastic material together with an oxygen scavenger, such as Ageless (Mitsubishi Gas Chemical), in order to prevent denaturation of the infusion liquids during storage. The packing of the outer bag with the container is carried out by inert gas (nitrogen for example)-charged packaging or vacuum packaging.

According to the above method, the infusion liquid containing a fat emulsion and sugars to be included in the first compartment 2 can be prepared by various methods. For example, sugars may be added to the fat emulsion prepared by the above-described method and may be added in advance at the time of preparation of the fat emulsion. The composition of the infusion liquid containing a fat emulsion and sugars can be varied depending on the concentration of the infusion liquid to be enclosed in the second compartment 3 (that is, the infusion liquid containing amino acids and electrolytes), the volumetric ratio of the liquids to be incorporated into the first and second compartments, and the like. A preferred example of the composition may consist of a fat in an amount of from approximately 0.1 to 30%, preferably from approximately 1 to 20%, more preferably from approximately 2 to 10%, an emulsifying agent in an amount of from approximately 0.01 to 10%, preferably from approximately 0.05 to 5%, more preferably from approximately 0.1 to 1%, sugars in an amount of from approximately 5 to 60%, preferably from approximately 7 to 40%, more preferably from approximately 10 to 30% and water in an appropriate amount.

The infusion liquid containing amino acids and electrolytes to be included in the second compartment 3 can be prepared by various means, for example, by dissolving various amino acids and electrolytes in purified water such as water for injection. The composition of the infusion liquid containing amino acids and electrolytes can be varied depending on the concentration of the infusion liquid to be enclosed in the first compartment 2 (that is, an infusion liquid containing a fat emulsion and sugars), the volumetric ratio of liquids to be injected into the first compartment 2 and the second compartment 3, and the like. A preferred example of the composition may consist of amino acids in a total amount of from approximately 1 to 15%, preferably from approximately 2 to 13%, more preferably from approximately 3 to 12% and, as electrolytes, approximately 80 to 120 mEq/l of sodium, approximately 70 to 100 mEq/l of chlorine, approximately 10 to 50 mmol/l of phosphorus, approximately 2 to 40 μmol/l of zinc and approximately 40 to 120 mEq/l of acetic acid, in addition to a suitable quantity of water.

The pH value of the alimentative infusion liquid of the present invention is adjusted to from 6.3 to 7.3, preferably from approximately 6.5 to 7.0, in order to reduce irritation to the living body. Especially, when a phosphoric ester of a polyhydric alcohol or a sugar or a salt of the ester is used as the source of phosphorus, precipitation can be effectively prevented even at a relatively high pH value.

Various acidic materials, preferably organic acids, can be used as agents for adjusting the pH of the infusion liquids as long as they are physiologically acceptable. Examples of the organic acids include citric acid, gluconic acid, lactic acid, malic acid, maleic acid and malonic acid. Organic acids having chelating capacity against divalent metal ions are preferably used, with citric acid being particularly preferred.

The above pH adjusting agent can be added to the infusion liquid at an appropriate time, but it is preferably added in advance to one or two or more of the infusion liquids including the sugar infusion liquid in an appropriate amount. For example, in the container filled with the infusion liquids as shown in FIG. 1, the pH adjusting agent may be added to the infusion liquid in the first compartment, the infusion liquid in the second compartment or both thereof. Particularly, the pH value is adjusted to 5.5 to 6.5 in the first compartment, and 6.5 to 7.5 in the second compartment.

The alimentative infusion liquid of the present invention has the titratable acidity of 8.5 mEq/l or below, preferably 2.0 mEq/l or below. The term "titratable acidity" as used herein means the amount (unit: mEq/l) of an acid or a base (in general, hydrochloric acid is used as the acid, while sodium hydroxide is used as the base) required for adjusting the pH value of the infusion liquid to 7.0. The titratable acidity is not adjusted artificially but determined spontaneously depending on the components constituting the infusion liquid and concentrations thereof. Because of having a low titratable acidity, the infusion liquid of the present invention rapidly comes to equilibrium with the pH value of the blood after the administration to a living body, which prevents troubles such as angialgia.

The alimentative infusion liquid of the present invention may contain an anti-coloring agent (for example, thioglycerol, dithiothreitol) in order to prevent coloring at the time of sterilization or during storage. Such an anti-coloring agent is usually added in an amount of about 1% or less. Although the anti-coloring agent may be added at any step without restriction, it is preferably added to one or two or more infusions, such as a sugar infusion liquid, in advance. In the case of the container as shown in FIG. 1, for example, the anti-coloring agent may be added to either the infusion liquid in the first compartment, the infusion liquid in the second compartment or both of them.

The alimentative infusion liquid of the present invention may further contain vitamins (for example, vitamin A, vitamin Bs, vitamin C, vitamin Ds, vitamin Es, vitamin Ks). Furthermore, the infusion liquid in the first compartment may contain a buffer agent such as L-histidine or tris (hydroxy-methyl)aminomethane. Such an additive is usually used in an amount of about 1% or less. If necessary, the infusion liquid of the present invention may further contain a stabilizer such as a sulfite or a bisulfite of sodium hydrogensulfite. The stabilizer is usually added in an amount of about 0.05% or less.

The alimentative infusion liquid of the present invention thus obtained has an excellent preservability. Namely, it can be stored for a prolonged period of time without showing precipitation, phase-separation, denaturation, coloring, etc.

The alimentative infusion liquid of the present invention is administered to a patient via a peripheral vein either as such or after diluting with water and either alone or in the form of a mixture with medicines, if necessary. In the field of internal medicine, the infusion liquid of the present invention can be used for alimentation for a short period. In particular, it is applicable to the alimentation for patients with cancer at the terminal stage, those with insufficient oral alimentation and those with temporary cut-off of oral alimentation. In the field of surgical medicine, the infusion liquid of the present invention is useful in, for example, pre- and postoperative alimentation.

Figure 1:
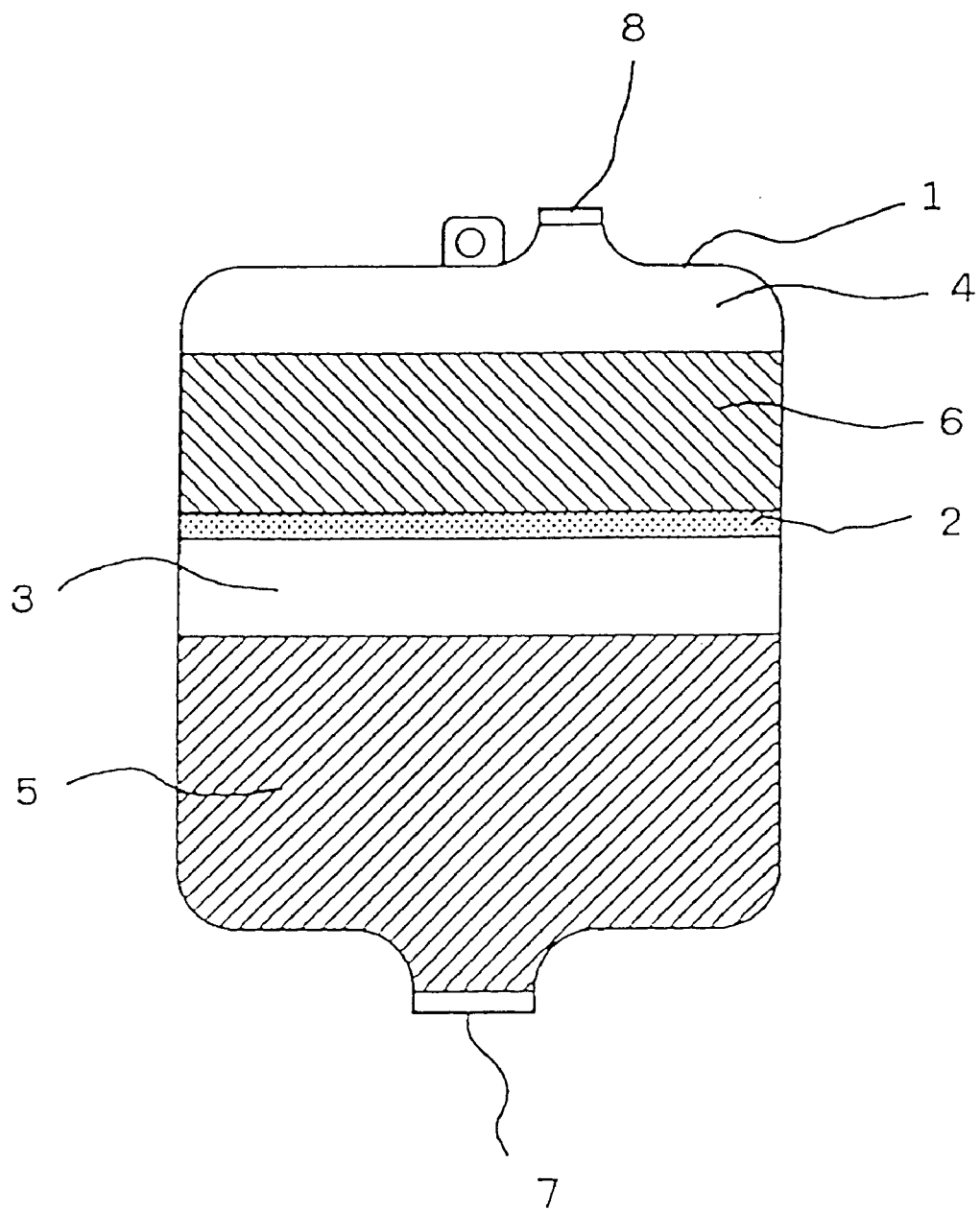
FIG. 1 schematically shows a container used for preparation of the alimentative infusion liquid of the present invention.

Definition of symbols:

1: container, 2: separation part, 3: first compartment, 4: second compartment, 5: infusion liquid in the first compartment, 6: infusion liquid in the second compartment, 7 and 8: ports.

BEST MODE FOR PRACTICE OF THE INVENTION

The present invention will be described in further detail with reference to Examples and Test Examples, but is not construed to be limited thereto.

EXAMPLE 1

(1) Preparation of Infusion Liquid Containing Fat Emulsion and Sugars

To water were added 266.7 g of soy bean oil, 38.4 g of egg yolk phospholipid and 1,000 ml of a 60% glucose aqueous solution. The resulting mixture was preliminarily emulsified using a mixer. Water was added thereto to make the total volume 1,333 ml, thereby obtaining a crude emulsion. The resulting emulsion was emulsified using a Manton-Gaulin homogenizer (15M-8TA, manufactured by Gaulin) until the mean particle diameter became 0.17 μm or less. Eight ml of a 2% L-histidine aqueous solution and water were added to 403.8 ml of the thus obtained emulsion to make the total volume 1,600 ml. The composition of the thus-obtained infusion preparation is shown in Table 1.

TABLE 1

| Component | Amount (g) |
| --- | --- |
| Soybean oil | 50.5 |
| Egg yolk phospholipid | 7.27 |
| Glucose | 113.6 |
| L-Histidine | 0.10 |
| Water for injection | amount necessary for making total volume 1,000 ml |

(2) Preparation of Infusion Liquid Containing Amino Acids, Electrolytes and Vitamins Amino acids and electrolytes shown in Table 2 and Table 3 were added to and dissolved in water for injection which was maintained at about 80° C. under a stream of nitrogen gas so as to give the respective concentrations. The pH value was adjusted to pH 7.0 with citric acid.

TABLE 2

| Component | Concentration (per liter) |
| --- | --- |
| L-Isoleucine | 5.77 g |
| L-Leucine | 10.09 g |
| L-Valine | 5.77 g |
| L-Lysine · HCl | 7.21 g |
| L-Methionine | 2.88 g |
| L-Phenylalanine | 5.77 g |
| L-Threonine | 4.33 g |
| L-Tryptophan | 0.87 g |
| L-Arginine | 7.57 g |
| L-Histidine | 3.60 g |
| Glycine | 3.82 g |
| L-Alanine | 6.13 g |
| L-Proline | 4.33 g |
| L-Aspartic acid | 1.08 g |
| L-Serine | 2.16 g |
| L-Tyrosine | 0.36 g |
| L-Glutamic acid | 1.08 g |
| N-Acetyl-L-cysteine | 0.72 g |

TABLE 3

| Component | Concentration (per liter) |
| --- | --- |
| Sodium chloride | 1.719 g |
| Potassium chloride | 0.877 g |
| Magnesium sulfate.7H$_2$O | 1.087 g |
| Calcium gluconate.H$_2$O | 1.978 g |
| Dipotassium glycerophosphate (50% solution) | 11.680 g |
| Anhydrous sodium acetate | 6.032 g |
| Zinc sulfate.7H$_2$O | 4.230 mg |

(3) Sterilization and Preparation of the Alimentative Infusion Liquid of the Present Invention A polyethylene container having a structure as shown in FIG. 1 was used. The infusion liquid (660 ml) containing the fat emulsion and the sugar obtained in the above (1) was injected into the first compartment 3 of the container 1 having the peelable separation part 2 from the port 7 with nitrogen gas charging, subsequently sealing the port 7. In the same manner, 340 ml of the infusion liquid containing the amino acids and the electrolytes obtained above was injected into the second compartment 4 from the port 8 with nitrogen gas charging, subsequently sealing the port 8. The thus-prepared container 1 in which each infusion liquid was enclosed was sterilized by autoclaving at 110° C. for 30 minutes, followed by cooling to room temperature.

After the sterilization, the separation part 2 was peeled and the infusion liquid in the first compartment 3 was mixed with the infusion liquid in the second compartment 4 thoroughly to obtain the alimentative infusion liquid of the present invention. The thus-obtained infusion liquid had the following composition.

TABLE 4

| Composition (per 1 liter) | |
| --- | --- |
| Fat | |
| Soybean oil | 33.3 g |
| Egg yolk phospholipid | 4.8 g |
| Sugar | |
| Glucose | 75.0 g |

TABLE 4-continued

Composition (per 1 liter)

| Amino acids | | |
|---|---|---|
| L-Isoleucine | 1.96 | g |
| L-Leucine | 3.43 | g |
| L-Valine | 1.96 | g |
| L-Lysine · hydrochloride | 2.45 | g |
| L-Methionine | 0.98 | g |
| L-Phenylalanine | 1.96 | g |
| L-Threonine | 1.47 | g |
| L-Tryptophan | 0.30 | g |
| L-Arginine | 2.57 | g |
| L-Histidine | 1.22 | g |
| Glycine | 1.30 | g |
| L-Alanine | 2.08 | g |
| L-Proline | 1.47 | g |
| L-Aspartic acid | 0.37 | g |
| L-Serine | 0.73 | g |
| L-Tyrosine | 0.12 | g |
| L-Glutamic acid | 0.37 | g |
| N-Acetyl-L-cysteine | 0.24 | g |
| Electrolytes | | |
| Sodium | 35.0 | mEq |
| Potassium | 20.0 | mEq |
| Calcium | 3.0 | mEq |
| Magnesium | 3.0 | mEq |
| Chlorine | 27.4 | mEq |
| Phosphorus | 8.0 | mmol |
| Zinc | 5.0 | μmol |
| Acetic acid | 25.0 | mEq |
| Others | | |
| Citric acid | 1.401 | g |
| pH | 6.8 | |
| Titratable acidity (mEq/l) | 1.06 | |

(4) Stability Test of the Infusion Liquid of the Present Invention

The infusion liquid obtained in the above (3) was preserved at 25° C. for 48 hours and the changes of appearance, mean particle diameter of the fat emulsion and turbidity were determined. The results are shown in Table 5. The mean particle diameter of the fat emulsion was measured by the light scattering method, and turbidity was measured in terms of absorbance at 620 nm (1-cm cell).

TABLE 5

| | Storage time | | |
|---|---|---|---|
| Test item | Immediately after mixing | After 24 hr. | After 48 hr. |
| Inventive preparation | | | |
| Appearance | No change | No change | No change |
| Mean particle diameter | 0.13 μm | 0.13 μm | 0.13 μm |
| Turbidity | 0.042 | 0.041 | 0.041 |
| pH | 6.85 | 6.85 | 6.85 |

As shown in Table 5, no change was observed in appearance, mean particle diameter and turbidity. The results reveal that the infusion liquid of the present invention has high stability.

Pharmacological Test Example 1

The infusion liquid obtained in Example 1 was subjected to a vasostimulation test using rabbits. The test conditions and the test method are as specified below. As a control, commercially available Ringer's solution was used.

(1) Test Conditions
  (i) Administration route: via retroauricular vein in the marginal part of right auricle.
  (ii) Administration rate: 1 ml/kg/min.
  (iii) Dose: 40 ml/kg.
  (iv) Administration manner: continuous dripping once a day for 5 days.
  (v) Number of animals: three.

(2) Test Method
  (i) Observation of administration site
  For each case, the blood vessel at the administration site and the tissue therearound were observed with the naked eye and palpation 24 hours after the first administration, before the subsequent administrations and before dissection. Thus the thrombus formation and inflammation were evaluated each in four grades in accordance with the following criteria.

| | Finding | Score |
|---|---|---|
| Criteria for thrombus formation: | not formed | 0 |
| | small thrombus (1–4 mm) | 1 |
| | medium thrombus (5–14 mm) | 2 |
| | large thrombus ($\geq$15 mm) | 3 |
| Criteria for inflammation: | no change | 0 |
| | slight inflammation ($\leq$3 cm around hemostatic site) | 1 |
| | medium inflammation ($\leq$⅓of auricle around hemostatic site) | 2 |
| | severe inflammation ($\geq$½of auricle) | 3 |

(ii) Pathologic Histological Examination

On the next day of the final administration, the administration site of each case was photographed under thiopental sodium anesthesia. Then, the animal was slaughtered due to blood loss and the auricle was excised. The auricle was fixed with a 10% formalin buffer solution (neutral). The blood vessel at the administration site and the part therearound [about 20 mm from the attainment site of the injection needle toward the ear root (i.e., the heart side)] were taken out, stained with hematoxylin and eosin in accordance with the conventional method and observed under a light microscope.

To evaluate the vasostimulation, the observation area were divided into three parts (i.e., the vein, the tissue around the vein and the skin) followed by the pathological evaluation of each part. Changes were evaluated in four grades, namely, slight (±), light (+), moderate (++) and severe (+++).

The results of the above-mentioned tests are as follows.
(i) Results of Observation with Naked Eye

| Medicine | Infusion liquid of invention | | | | Commercially available Ringer's solution | | | |
|---|---|---|---|---|---|---|---|---|
| Score | 0 | 1 | 2 | 3 | 0 | 1 | 2 | 3 |
| Thrombus (no. of animals) | 3 | 0 | 0 | 0 | 3 | 0 | 0 | 0 |
| Inflammation (no. of animals) | 3 | 0 | 0 | 0 | 1 | 2 | 0 | 0 |

In the case of the commercially available Ringer's solution (manufactured by Otsuka Pharmaceutical Co., Ltd.; listed in the Pharmacopoeia of Japan), slight inflammation was observed, though no thrombus was formed.

In contrast, neither thrombus nor inflammation was observed in the case of the infusion liquid of the present invention.

(ii) Results of Histological Examination

| Medicine | Infusion liquid of invention | | | Commercially available Ringer's solution | | |
|---|---|---|---|---|---|---|
| Animal no. | 1 | 2 | 3 | 1 | 2 | 3 |
| Vein: | | | | | | |
| Endotheliocytosis | ± | – | – | – | – | – |
| Thrombus formation | – | – | – | – | – | + |
| Tissue around vein: | | | | | | |
| Cellular infiltration | ± | – | – | – | – | – |
| Hemorrhage | – | – | – | – | + | – |
| Fibrogenesis | – | – | – | – | – | – |
| Skin: | | | | | | |
| Acanthosis | – | – | – | – | – | – |

Thus the results of the histological examinations indicate that the infusion liquid of the present invention is so excellent as to be free from vasostimulation.

Industrial Applicability

As described above, the alimentative infusion liquid of the present invention, which contains sugars, amino acids, electrolytes and a fat emulsion, does not suffer from precipitation, phase-separation, denaturation, coloring, etc., though it contains the above-mentioned components. Because of having a pH value regulated to a definite level and a low titratable acidity, it causes no trouble such as angialgia when administered via a peripheral vein. According to the present invention, therefore, a hyperalimentative infusion liquid containing sugars, amino acids, electrolytes and a fat emulsion can be administered via a peripheral vein and an elevated caloric value can be supplied compared with the conventional infusion liquids for administration via a peripheral vein. Moreover, it is not necessary to blend sugars, amino acids, electrolytes and a fat emulsion before using, which makes it possible to simplify the procedure and to prevent contamination with bacteria during blending.

We claim:

1. An alimentative infusion liquid for administration through a peripheral vein containing sugars, amino acids, electrolytes a fat emulsion, which has a pH of 6.3 to 7.3 and a titratable acidity of 8.5 mEq/l or below, does not cause angialgia and is excellent in stability and preservability.

2. The alimentative infusion liquid according to claim 1, which has the following composition:

| | |
|---|---|
| fat | 30–40 g/l |
| emulsifying agent | 4–6 g/l |
| sugar | 60–90 g/l |
| L-isoleucine | 1–3 g/l |
| L-leucine | 2.5–4.5 g/l |
| L-valine | 1–3 g/l |
| L-lysine | 1–3 g/l |
| L-methionine | 0.5–1.5 g/l |
| L-phenylalanine | 1–3 g/l |
| L-threonine | 0.5–2.5 g/l |
| L-tryptophan | 0.1–1 g/l |
| L-arginine | 1.5–3.5 g/l |
| L-histidine | 0.5–2.5 g/l |
| glycine | 0.5–2.5 g/l |
| L-alanine | 1–3 g/l |
| L-proline | 0.5–2.5 g/l |
| L-aspartic acid | 0.1–1 g/l |
| L-serine | 0.1–2 g/l |
| L-tyrosine | 0.05–0.25 g/l |
| L-glutamic acid | 0.3–0.6 g/l |
| L-cysteine | 0.01–0.5 g/l |
| sodium | 30–40 mEq/l |
| potassium | 15–25 mEq/l |
| calcium | 1–5 mEq/l |
| magnesium | 1–5 mEq/l |
| chlorine | 25–30 mEq/l |
| phosphorus | 5–15 mmol/l |
| zinc | 1–10 μmol/l |
| acetic acid | 15–35 mEq/l. |

3. The alimentative infusion liquid according to claim 1, wherein the fat emulsion has a mean particle diameter of 0.17 μm or less.

4. The alimentative infusion liquid according to claim 3, wherein the fat emulsion is the product of emulsifying fat with glycerol and/or glucose.

5. The alimentative infusion liquid according to claim 2, wherein phosphorus is contained as a phosphoric ester of a polyhydric alcohol or a sugar or a salt of the ester.

6. The alimentative infusion liquid according to claim 2, produced by adjusting the pH value with citric acid.

7. The alimentative infusion liquid according to claim 1, which includes at least one electrolyte component selected from the group consisting of sodium chloride, sodium lactate, sodium acetate, sodium sulfate, sodium glycerophosphate, potassium chloride, potassium glycerophosphate, potassium sulfate, potassium acetate, potassium lactate, calcium gluconate, calcium chloride, calcium glycerophosphate, calcium lactate, calcium pantothenate, calcium acetate, magnesium sulfate, magnesium chloride, magnesium glycerophosphate, magnesium acetate, magnesium lactate, zinc sulfate, zinc chloride, zinc gluconate, zinc lactate and zinc acetate.

8. The alimentative infusion liquid according to claim 1, comprising in the fat emulsion, at least one fat or oil selected from the group consisting of plant oils, fish oils, medium-chain fatty acid triglycerides and chemically defined triglycerides.

9. The alimentative infusion liquid according to claim 8, wherein the fat emulsion comprises a soybean oil with an egg yolk phospholipid as an emulsifying agent.

10. In a method for nourishing a patient requiring an alimentative infusion liquid, the improvement comprising administering an alimentative infusion liquid comprising sugars, amino acids, electrolytes and a fat emulsion, said liquid having a pH of 6.3 to 7.3 and a titratable acidity of 8.5 mEq/l or below, said administering being via a peripheral vein and without causing crisis of said peripheral vein.

* * * * *